(12) United States Patent
Eells et al.

(10) Patent No.: US 9,226,734 B2
(45) Date of Patent: Jan. 5, 2016

(54) CLOSED SIDE-SAMPLING BIOPSY DEVICE

(75) Inventors: Robert Eells, Bloomington, IN (US); Jeffry S. Melsheimer, Springville, IN (US); Grant T. Hoffman, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 348 days.

(21) Appl. No.: 13/428,038

(22) Filed: Mar. 23, 2012

(65) Prior Publication Data

US 2012/0245487 A1   Sep. 27, 2012

Related U.S. Application Data

(60) Provisional application No. 61/467,105, filed on Mar. 24, 2011.

(51) Int. Cl.
*A61B 10/00* (2006.01)
*A61B 10/02* (2006.01)

(52) U.S. Cl.
CPC ..... *A61B 10/0275* (2013.01); *A61B 2010/0208* (2013.01)

(58) Field of Classification Search
CPC ................. A61B 10/0275; A61B 2010/0208; A61B 10/0266; A61B 10/0283
USPC ................... 600/562–568; 606/167, 170, 171
See application file for complete search history.

(56) References Cited

U.S. PATENT DOCUMENTS

| | | |
|---|---|---|
| 5,133,359 A | 7/1992 | Kedem |
| 5,423,824 A | 6/1995 | Akerfeldt et al. |
| 5,488,958 A | 2/1996 | Topel et al. |
| 5,601,585 A | 2/1997 | Banik et al. |
| 5,709,697 A | 1/1998 | Ratcliff et al. |
| 5,810,826 A | 9/1998 | Akerfeldt et al. |
| 5,916,229 A | 6/1999 | Evans |
| 5,961,534 A | 10/1999 | Banik et al. |
| 6,083,237 A | 7/2000 | Huitema et al. |
| 6,752,769 B2 * | 6/2004 | Alberico ........................ 600/570 |
| 6,899,685 B2 | 5/2005 | Kermode et al. |
| 7,033,357 B2 | 4/2006 | Baxter et al. |
| 7,635,340 B2 | 12/2009 | Vetter et al. |
| 2007/0161925 A1 * | 7/2007 | Quick et al. ................... 600/564 |
| 2011/0313316 A1 * | 12/2011 | Ranpura et al. ............... 600/566 |
| 2012/0172752 A1 * | 7/2012 | Ranpura et al. ............... 600/567 |

* cited by examiner

*Primary Examiner* — Max Hindenburg
*Assistant Examiner* — Jonathan M Foreman
(74) *Attorney, Agent, or Firm* — Woodard, Emhardt, Moriarty, McNett & Henry LLP

(57) ABSTRACT

Among other things, there are disclosed embodiments of a biopsy device using relative rotational motion to obtain a full-core biopsy sample. Inner and outer tubular members are provided connected to a handle. Each member includes a slit, and the members are rotatable with respect to each other. The device is inserted into a patient to a sampling site, and with the slits co-oriented, is extended into the sampling site. Tissue enters the tubular members through the slits, and one or both members are rotated to cut off and enclose tissue within the inner tubular member.

21 Claims, 7 Drawing Sheets

CLOSED SIDE-SAMPLING BIOPSY DEVICE

REFERENCE TO RELATED APPLICATION

This application claims the benefit of U.S. Provisional Patent Application No. 61/467,105, filed Mar. 24, 2011, which his hereby incorporated by reference.

The present disclosure relates to medical devices for obtaining tissue samples. More particularly, the disclosure relates to a device easily insertable into a patient to an area of tissue from which a sample is to be taken, that more accurately obtains such a sample.

BACKGROUND

It is known to acquire one or more samples of tissue when particular localized medical problems are suspected, in order to test such samples and determine whether or to what extent a problem exists. For example, if a physician discovers a growth within soft tissue of a patient and wishes to test whether it is benign or cancerous, a deep biopsy sample of the soft tissue can be acquired. For such cases, biopsy devices have been developed that can be passed through skin, muscle and/or other tissues or body-walls and into the area of tissue of concern to the physician. The device's distal end cuts out a sample, e.g. a "core-sample," of the suspicious tissue.

Various forms of existing biopsy devices use a moving mandrel or cannula that facilitates movement through tissue and cutting of a sample from surrounding tissue, so that the sample may be withdrawn with the device. A quick, longitudinal movement of a cannula, for example, is generally used to cut through tissue faster than the tissue can be moved forward or out of the way by the device. Depending on the particular type of device, problems that exist with such biopsy devices can include an inability to obtain a full core of tissue. For instance, a stylet or cannula may shoot forward beyond the tissue of interest or other sampling area, or may cut only a portion of a cylinder, thus not providing a full 360-degree sample. A full core of tissue has advantages over smaller or more-limited samples in providing sufficient tissue for assay, in determining any changes or alterations in tissue at various positions in the sample (e.g. equidistant locations in various directions from the sampling path), and in noting changes in tissue as it extends from a center of the sampling area or path. Inaccuracies in the physician's or other operator's anticipation as to exactly how far the device's distal end will advance during sampling can result in the target tissue being overshot or undershot. If the operator does not know with significant accuracy the depth of the tissue of interest, or does not assess where the tissue of interest is with respect to the cutting area of the device, the insertion of the device may result in the cutting area being partially or completely outside of the tissue of interest, resulting in acquisition of tissue that does not provide the information the physician is seeking. Additionally, there may be difficulties in providing speed and/or power of forward thrust for the cannula necessary to move through and shear tens of millimeters of tissue cleanly, regardless of the tissue's density. Forward-thrusting biopsy devices, if not placed properly, if they have less-sharp edges, or if they are under-powered in propelling the cannula forward, can press tissue forward rather than shearing through it. Common results in such cases are less or no sample within the device, or crushing some or all of the tissue. It has been found that the physical state of the sample can affect its usefulness for assay or its ability to provide significant information relative to the health or other characteristics of the sample.

SUMMARY

Among other things, there is disclosed apparatus for obtaining a biopsy sample which includes first and second tubular members (e.g. metal needles or cannulas), with the second inserted within the first. Embodiments of the first cannula have a lumen surrounded by a lumen wall, a distal end with a sharp edge, and a slit beginning at a point proximal of the distal end and extending proximally. The lumen wall between the distal end and the slit may be smooth. The second cannula is within the first cannula's lumen, and it includes a lumen and a closed distal end tapering to a point. Embodiments of the second cannula have an outer diameter such that the second cannula has a close and rotatable fit with the lumen wall of the first cannula. The second cannula has a slit beginning at a point proximal of the tapering distal end and bounded by at least one sharpened edge. The cannulas have a first open relative position, in which the slits define an open passage from the exterior of the first cannula to the lumen of the second cannula, and a second closed position, in which the slits are rotationally offset from each other. Change between the first and second positions is accomplished by rotation of at least one of the cannulas.

In particular embodiments, the slits may be substantially congruent to each other, so that when the cannulas are in the first open relative position, the slits are substantially exactly aligned along their entireties. The second cannula can be rotatable around the central longitudinal axis of the first cannula, and the slits can be non-parallel (e.g. diagonal or helical) to that axis, or they can be parallel to that axis. In some embodiments, the distal end of the first cannula is closed, and the cannulas are configured so that the tapering distal end of the second cannula can engage the closed distal end of the first cannula. When the tapering distal end engages that closed distal end, the slits are relatively positioned in the first open relative position, the second closed relative position, or a position between them.

A handle can be provided for the cannulas. For example, a handle can have an inner portion and an outer portion, with the outer portion fixed to the first cannula and the inner portion fixed to the second cannula. Rotation of at least one of the handle portions with respect to the other may be used to shift the cannulas toward one of the open or closed relative positions. In some embodiments, an inner handle portion is rotatable with respect to an outer handle portion, and the inner handle portion is spring-biased, with the bias tending to hold the cannulas in a closed relative position. A triggering mechanism adapted to hold the inner handle portion in a cocked position against the bias can also be provided. The cocked position may correspond to the cannulas being in the open relative position, and release of the triggering mechanism allows the bias to rotate the second cannula within the first cannula.

The disclosure also includes an apparatus for obtaining a biopsy sample that includes a first tubular member having a distal end and a slit a distance proximally away from the distal end, and a second tubular member rotatably positioned within the first tubular member and having a slit with at least one sharpened lateral edge. A handle having a first portion attached to the first tubular member and a second portion attached to the second tubular member is also provided, and the handle can have a spring-bias and a triggering mechanism. The apparatus has a first uncocked configuration in which the slits do not overlap. In a second cocked configuration, the second tubular member and second handle portion are rotated from the first configuration against the bias so that the slits overlap and the triggering mechanism maintains that second configuration. Activation of the triggering mechanism when the apparatus is in the second configuration results in the bias rotating the second tubular member within the first tubular member to the first configuration.

One or more of a number of features can be included in particular embodiments. For example, at least one of the slits may be diagonal or helical. In the second configuration, the entirety of the slit of the second tubular member overlaps the slit of the first tubular member. The second tubular member can be adapted to be entirely withdrawn longitudinally from within the first tubular member to retrieve a sample within the second tubular member. In certain embodiments, each of the slits has a length measured along a longitudinal axis of their respective tubular members and a width measured perpendicular to the longitudinal axis of their respective tubular members. Such widths may be substantially constant and subtend an arc of more than 90 degrees but less than 180 degrees of their respective tubular members, or may subtend an arc of greater than 180 degrees and less than 270 degrees. The slit of the first tubular member may also have at least one lateral edge that is sharpened, with that sharpened lateral edge of the first tubular member's slit facing the sharpened lateral edge of the second tubular member's slit when the apparatus is in the second cocked configuration.

An embodiment of an apparatus for obtaining a biopsy sample may include a first cannula having a central lumen surrounded by a lumen wall, a distal end with a sharp edge, and a diagonal or helical slit beginning at a point proximal of the distal end and extending proximally, with the lumen wall between the distal end and slit being smooth. A second cannula having a lumen and a closed distal end tapering to a point is positioned within the lumen of the first cannula so that the second cannula's tapering distal end is within or extending from the distal end of the first cannula. The second cannula has an outer diameter such that it has a close and rotatable fit with the lumen wall of the first cannula. The second cannula also has a diagonal or helical slit beginning at a point proximal of the tapering distal end and bounded by at least one sharpened edge. The cannulas have a first open relative position, in which the first cannulas' slit lies over the entirety of the second cannula's slit and the slits define an open passage from the exterior of the first cannula to the lumen of the second cannula. The cannulas also have a second closed position, in which the slits are rotationally offset from each other and no part of the slits face each other. Change between the first position and the second position is accomplished by rotation of the second cannula with respect to the first cannula. A handle having a first portion fixed to the first cannula and a second portion fixed to the second cannula, with the second portion rotatable with respect to the first portion to rotate the second cannula with respect to the first cannula. The handle includes a spring biasing the second handle portion so that the cannulas are biased toward the second closed relative position, and a triggering mechanism adapted to hold one or both of the handle portions against the bias of the spring so as to hold the cannulas in the first open relative position.

In such embodiments, the distal end of the first cannula can be closed, and the tip of the second cannula can abut the distal end of the first cannula. Alternatively, the distal end of the first cannula is open, and the tip of the second cannula can face outward from the distal end of the first cannula and form with the distal end of the first cannula a leading insertion end of the apparatus. At least one of the distal end of the first cannula and the tip of the second cannula may include a marker that is at least one of radiopaque and echogenic.

Methods for manufacturing and using the apparatus embodiments are also disclosed. As an example of use, the apparatus may be in an uncocked state, with slits in each cannula offset from each other. The apparatus is inserted into the patient so that the distal end (e.g. the distal end of the outer cannula and/or the tapered or pointed end of the inner cannula) is at the border of or just inside the region of tissue to be sampled. The apparatus is cocked, so that the slits overlap each other and are held in that position. The apparatus is then forced into (or further into) the sampling region, and tissue enters the inner cannula lumen via the passage formed by the slits. When the desired length of sample has been obtained (i.e., when the apparatus has been forced a determined length into the tissue to be sampled), the apparatus is triggered. The cannulas rotate with respect to each other (e.g. the inner cannula rotates within a stationary outer cannula), cutting off the tissue within the inner cannula from surrounding tissue. That is, one or both cannulas may be rotated in a controlled manner (e.g. by a mechanism in a handle affixed to the proximal end of both cannulas). The slits in the cannulas are thus selectively either rotationally aligned (to form an opening), rotationally misaligned (e.g. up to or including 180 degrees), to close the opening to the inner lumen, or rotating (or rotatable) from open to closed (to encompass and shear tissue residing in the inner lumen) or from closed to open (to prime or cock the apparatus in use). The inner cannula is removed from the outer cannula, or the entire apparatus is removed from the patient, so that the sample can be retrieved and stored for later testing.

DESCRIPTION OF THE ILLUSTRATED EMBODIMENTS

Figure 1:
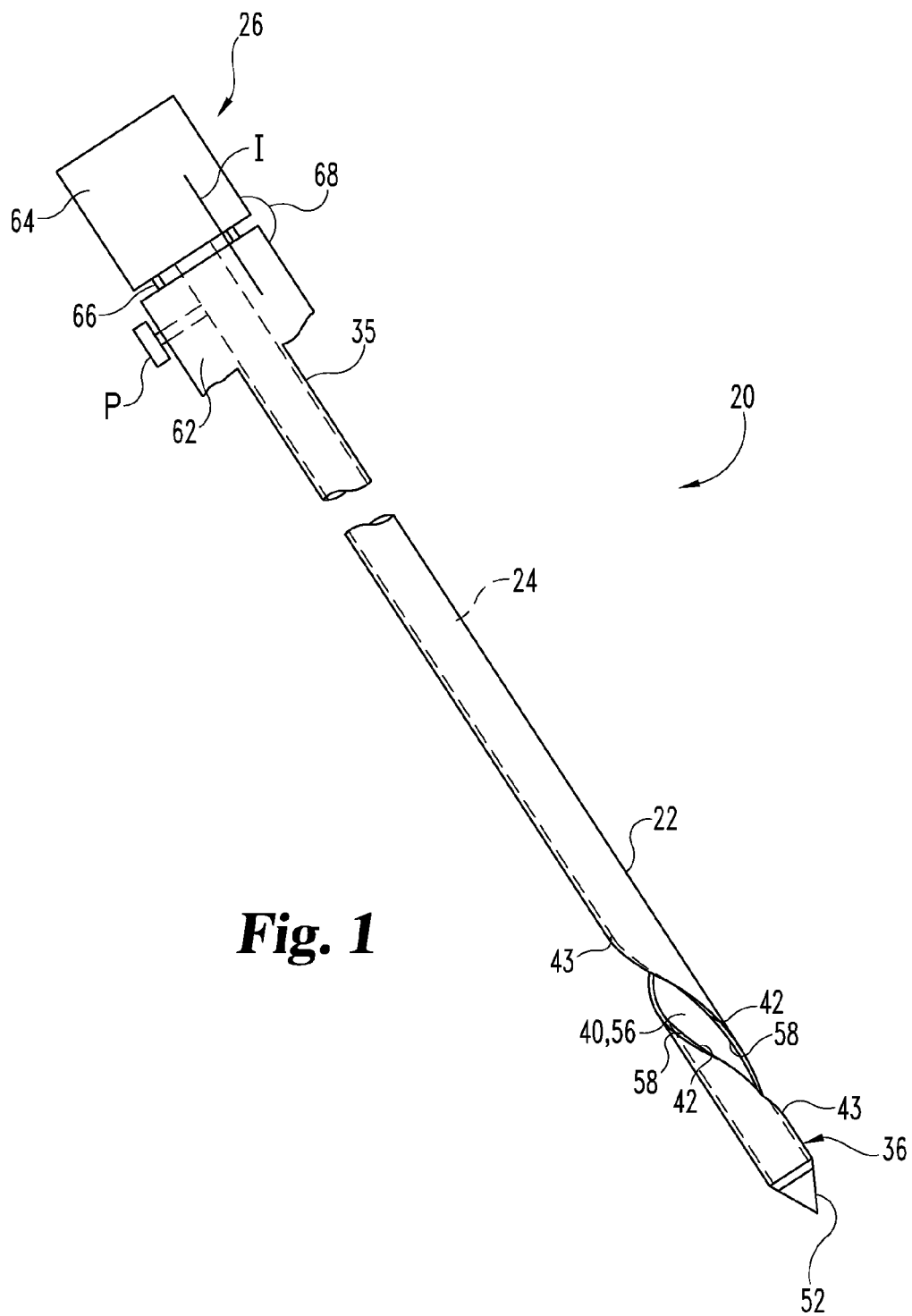
FIG. 1 is a side view of an embodiment of a biopsy device of the present disclosure.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated embodiments, and such further applications of the principles of the disclosure as illustrated therein being contemplated as would normally occur to one skilled in the art to which the disclosure relates.

Referring now generally to the drawings, there is shown an embodiment of a biopsy device 20. Device 20 includes a first outer cannula 22, a second inner cannula 24, and a handle portion 26 connected to each of the cannulas 22, 24. As will be further explained below, cannulas 22, 24 are configured so that on insertion into the body, a portion of tissue enters through the sides of cannulas 22 and 24 to occupy at least a portion of a lumen in cannula 24. Thereafter, one or both of cannulas 22 and 24 are rotated to sever the portion of tissue from surrounding tissue and maintain that portion of tissue within cannula 24.

Cannula 22 is a generally tubular member, having an outer surface 30 and an inner surface 32 that generally defines a lumen 34. In the illustrated embodiment, cannula 22 (and lumen 34) is substantially linear, having a central longitudinal axis. It will be understood that depending on the thinness of the wall of cannula 22 and the material of which it is made, cannula 22 may have some flexibility in use. As particular examples, cannula 22 may be formed from a tube of the type generally used for hypodermic needles, and may be of stainless steel, nickel-titanium alloy (Nitinol) or similar alloys or materials. In such embodiments, cannula 22 will have approximately the rigidity of hypodermic needles. Such hypodermic tubes can be initially formed to possess a sharpened distal end, perhaps with additional honing or polishing, or a sharpened end can be made by beveling to provide one or more sharp edges. A proximal end of the tube is affixed to a portion of handle 26, as further noted below. It will be understood that rather than forming cannula 22 from a hypodermic tube, a structure akin to such a tube may be manufactured of the noted materials or others that are sturdy and applicable to cutting substantially tubular profiles.

The illustrated embodiments of cannula 22 has a proximal end 35 attached to handle 26 and a distal end 36 with a beveled sharpened distal edge 38. Distal end 36 is shown in the drawings to be open, but there is no access to lumen 34 through or adjacent to sharpened edge 38 because of the intervening inner cannula 24 which occupies lumen 34. While an open distal end 36 provides advantages as will be discussed below, it will be understood that other embodiments of cannula 22 may include a closed distal end 36. Distal edge 38 is generally circular when viewed end-on in the illustrated embodiments, formed by a bevel that extends toward the central longitudinal axis of cannula 22 from all parts of outer surface 30 at distal end 36. In other embodiments cannula 22 may have a closed distal end with a full-bevel (i.e. planar) sharpened distal edge, so that no access to the inside of the cannula is possible via the distal end. In other respects, such a closed-end cannula is like cannula 22, e.g. having one or more sharpened forward and lateral edges to assist in cutting through tissue as discussed herein.

Figure 2A:
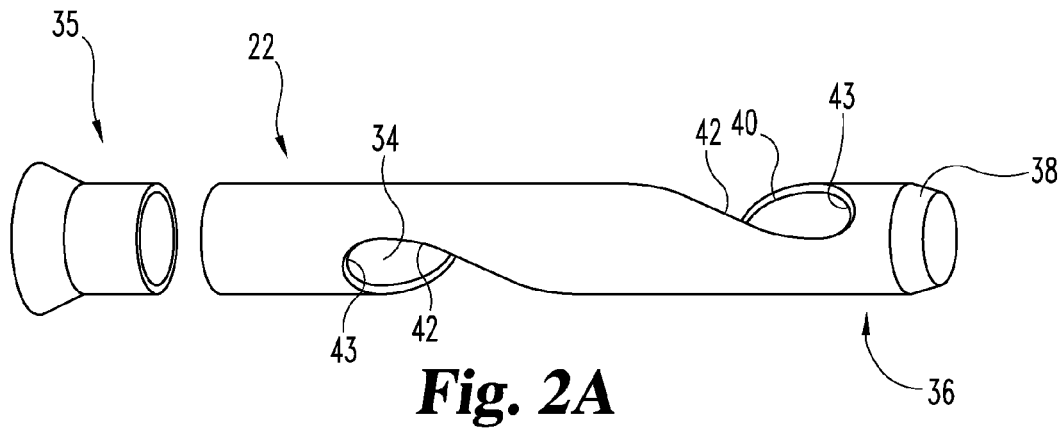
FIG. 2A is a perspective view of a portion of the embodiment shown in FIG. 1.

Cannula 22 further includes a slit 40 that originates at a point proximal of end 36. The illustrated embodiment shows a diagonal or helical slit 40 along cannula 22, bounded by lateral edges 42 and end edges 43. It is contemplated that slit 40 may be substantially longitudinal rather than diagonal or helical in other embodiments. A particular slit 40 has a width measured perpendicular to the longitudinal axis (i.e. between facing edges 42) that is constant and less than the diameter of cannula 22. That is, as indicated in FIG. 2A, the circumference C of outer surface 30 around cannula 22 from one edge 42 to another has an arc that is greater than 180 degrees, and in particular embodiments has an arc of between about 185 degrees and 270 degrees. An exemplary embodiment of cannula 22 has slit 40 beginning approximately 5 millimeters from end 36 and extending between 10 and 20 millimeters (about 15 millimeters in a particular example) proximally. If slit 40 is diagonal or helical, it may extend about 360 degrees around cannula 22, with its beginning or distal end being in one side of cannula 22 and its conclusion or proximal end in the same side of cannula 22, having twisted around at least approximately a whole circumference of cannula 22, as indicated in the illustrated embodiment. It will be understood that in other embodiments, slit 40 may twist around less than 360 degrees of cannula 22 (e.g. about half-way or 180 degrees around, or about three-quarters or 270 degrees around, as the size of cannula and the needed amount of biopsy tissue may require), or around more than 360 degrees around cannula 22. One or more of edges 42 and/or 43 are sharpened in certain embodiments, as by beveling or grinding, to assist in cutting through tissue, while in other embodiments such sharpening of edges 42 and 43 need not be done.

Within cannula 22 is cannula 24. Cannula 24, like cannula 22, is a generally tubular member, having an outer surface 44 and an inner surface 46 that generally defines a lumen 48. In the illustrated embodiment, cannula 24 (and lumen 48) is substantially linear, having a central longitudinal axis that is collinear with the central longitudinal axis of cannula 22. It will be understood that depending on the thinness of cannula 24 and the material of which it is made, cannula 24 may have flexibility or rigidity along with such characteristics of cannula 22. Cannula 24 may be formed or constructed in the same way or of the same materials as noted above for cannula 22, for the sake of ease and for the prevention of adverse reactions between dissimilar materials in the bodily environment. Nevertheless, it will be understood that different materials can be used for cannulas 22 and 24 in certain embodiments.

Figure 3A:
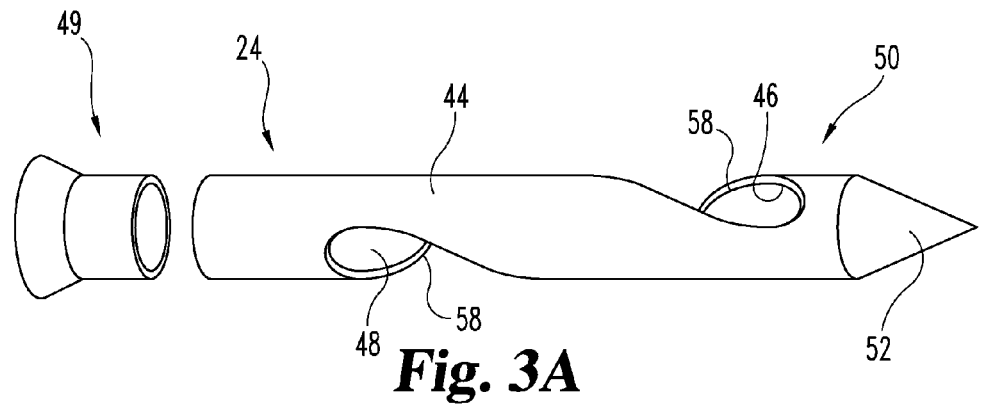
FIG. 3A is a perspective view of a portion of the embodiment shown in FIG. 1.
Figure 3B:
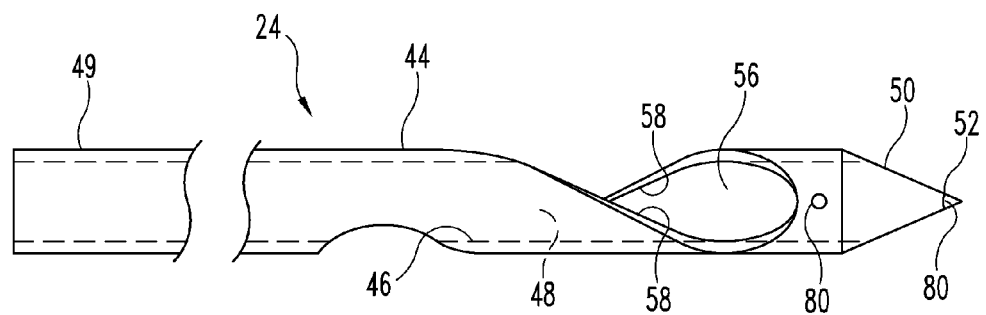
FIG. 3B is a side view of an inner portion of the embodiment shown in FIGS. 1 and 3A.

Cannula 24 is close-fitting within cannula 22, by which is meant that cannula 24 occupies lumen 34 of cannula 22 so that outer surface 44 of cannula 24 faces inner surface 32 of cannula 24 with a minimum of space between them and yet allowing cannulas 22 and 24 to readily or without significant impedance rotate with respect to each other. Accordingly, the illustrated embodiments show cannulas 22 and 24 with facing surfaces that are generally very smooth or unroughened, so that cannulas 22 and 24 can easily rotate with respect to each other. Cannula 24 has a proximal end 49 attached to handle 26 and a distal end 50 with a closed conical tip 52 resembling a sharpened pencil. In the embodiment of FIGS. 3A-B (and others), tip 52 is initially formed of a solid piece separate from the rest of cannula 24 that has been attached (e.g. by welding, gluing, interference fit, or the like) to the distal end of cannula 24. Alternatively, tip 52 may be initially formed on cannula 24, or may be generated through grinding and polishing techniques.

Such a "pencil-point" tip 52 fits with the distal end of cannula 22 as a continuation of sharpened distal edge 38 of outer cannula 22 in particular embodiments. In other embodiments of cannula 22, e.g. those in which its distal end 36 is closed, or is beveled along a single plane, tip 52 engages the inside of closed end 36 to impede further forward movement of cannula 24 with respect to cannula 22, or forms a complementary end with the bevel. For example, the conical shape of tip 52 may have substantially the same angle with respect to the longitudinal axis as an internal shape of end 36, so that the conical sides of tip 52 can contact closely or intimately with at least a substantial portion of the inside of end 36. Such a configuration provides a simple, straightforward indication in particular embodiments that cannula 24 is fully inserted or is in proper longitudinal position with respect to cannula 22. As one example, when cannula 24 is fully inserted, so that tip 52 engages end 36 of cannula 22, slits 40 and 56 (noted below) are exactly overlapping or occupy the same portion of the lengths of cannulas 22, 24. In embodiments of cannula 22 in which its distal end 36 is open, tip 52 (e.g. a portion of its conical sides) may engage a portion of the inner surface 32 of cannula 24, or may simply extend to or protrude from end 36. In such cases, where the angle of the conical sides of tip 52 are substantially the same as the bevel angle of end 36, a portion of tip 52 extending from cannula 22 presents a surface that moves tissue out of the way during insertion into a patient, as further noted below. Where end 36 is open, tip 52 fills lumen 34 so that during insertion little or no tissue or bodily matter enters lumen 34 via the distal opening of cannula 22.

Figure 4:
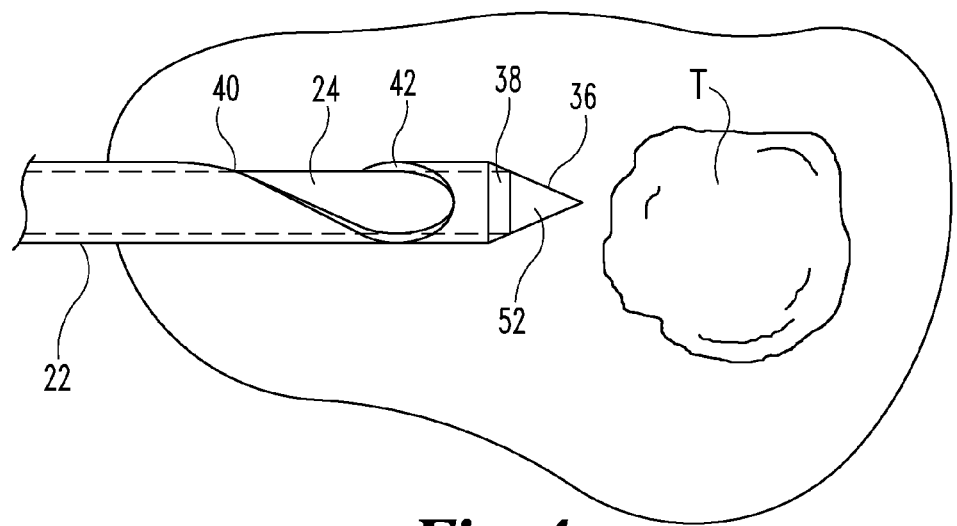
FIG. 4 is a side view of a portion of the embodiment of FIG. 1 in an uncocked condition during a particular use.
Figure 5:
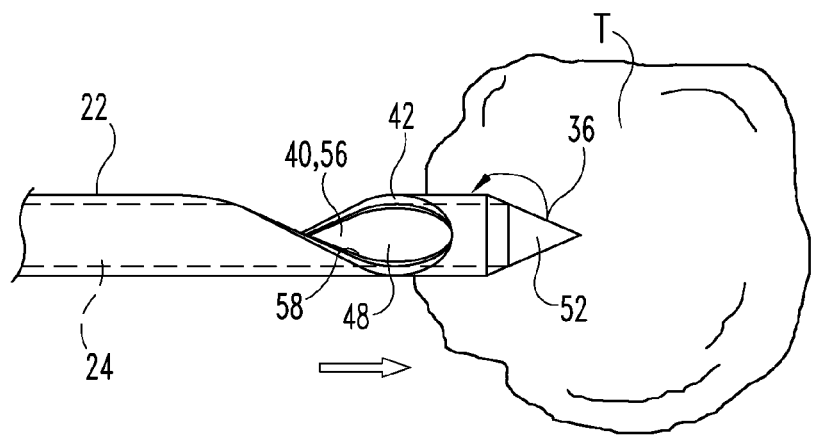
FIG. 5 is a side view as in FIG. 4 in a cocked condition.
Figure 6:
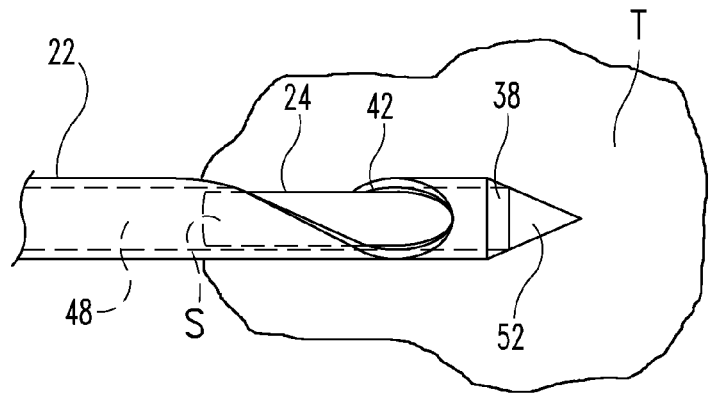
FIG. 6 is a side view as in FIG. 4 in a released or uncocked condition with a biopsy sample obtained.
Figure 7:
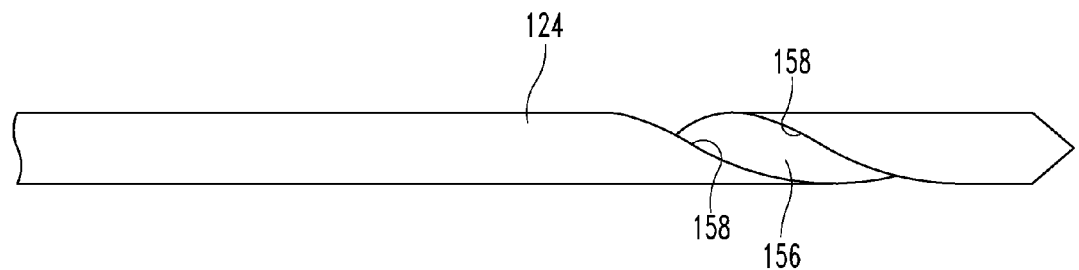
FIG. 7 is a side view of another embodiment of a part that can be used with the embodiment shown in FIG. 1.

Cannula 24 further includes a slit 56 that allows entrance to or communicates with lumen 48 and corresponds to slit 40 of outer cannula 22. Slit 56 may have substantially the same configuration as slit 40. For example, in the illustrated embodiment in which slit 40 is diagonal, slit 56 is also diagonal and is of approximately the same length and travels about the same distance around cannula 24 as slit 40 travels around cannula 22. In particular cases, slit 56 is substantially identical to slit 40 and is positioned and configured in cannula 22 so that when cannulas 22 and 24 are in a particular relative position, slit 40 is directly over slit 56 to form a uniform opening into lumen 48 of cannula 24. For example, slits 40 and 56 may be translational or longitudinally co-extant (e.g. FIGS. 1-3) when cannula 24 is fully inserted in cannula 24. As discussed further below, at least one of cannulas 22, 24 are rotatable with respect to each other between a position in which slit 40 is directly over slit 56 (e.g. FIG. 5) and a position in which the wall of cannula 22 covers slit 56 (e.g. FIG. 4). This close or uniform correspondence between slits 40 and 56 allows the maximum amount of tissue to enter through slits 40 and 56 into lumen 48 of cannula 24, and allows edges 42 and 58 to function as shears when rotated against intervening tissue.

Slit 56 further has at least one of its lateral edges 58 sharpened to present a cutting edge. For example, edge(s) 58 may be beveled so that one or both come to a sharp point at or adjacent to inner surface 46 of cannula 24. As noted below, turning one or both of cannulas 22, 24 relative to each other completely cuts a tissue sample from surrounding tissue, and if the relative turning is always in one specific rotational direction, then only one edge 58 may be sharpened. If, however, final cutting can occur by rotating one or both of cannulas 22 and 24 in either direction, then both lateral edges 58 may be sharpened.

Slits 40 and 56 may be formed in the respective cannulas 22 and 24 using techniques and devices such as computer numerical controlled (CNC) lasers, electric discharge machining (EDM), or electro-abrasive machining. If slit 40 is cut or formed so that its edge(s) are sharpened, it may be done by beveling during formation, or such edge(s) can be sharpened or beveled in secondary operations by abrasives, machining, or electro-chemical means. The sharpened edge(s) (e.g. lateral edges 58) of slit 56 can be made as indicated above with respect to slit 40.

Figure 2B:
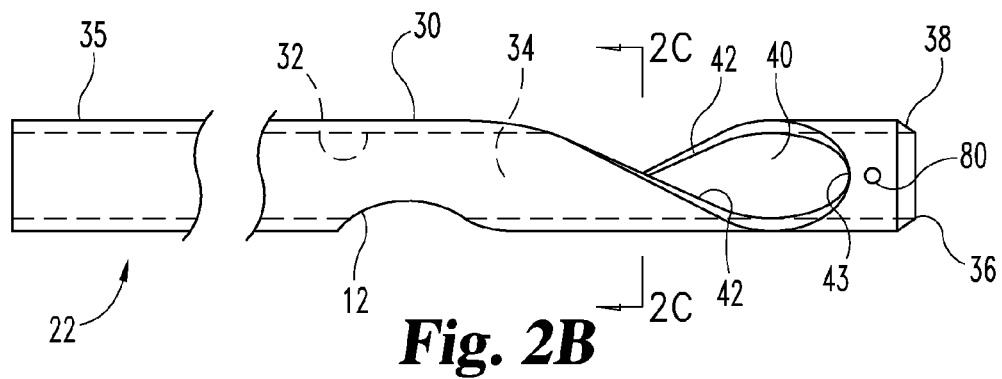
FIG. 2B is a side view of an outer portion of the embodiment shown in FIGS. 1 and 2A.
Figure 2C:
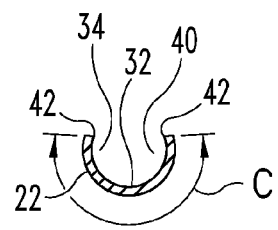
FIG. 2C is a cross-sectional view taken along the lines 2C-2C of FIG. 2B and viewed in the direction of the arrows.

Handle 26 is indicated schematically in FIG. 1, and it provides hand control of device 20, with cannula 22 and 24 attached to respective portions of handle 26. Handle 26 controls the rotational position of cannulas 22, 24, and is used to cause them to rotate relative to one another in a prescribed manner. Handle 26 is optionally built to contain a cocking lever or indicator I and/or a flushing or aspiration port P. Handle 26 permits rotation of one or both of cannulas 22, 24 with respect to the other so as to fully cut a measure or sample of tissue. In a particular embodiment, handle 26 has an outer or distal portion 62 fixed directly to proximal end 35 of cannula 22 and an inner or proximal portion 64 fixed directly to proximal end 49 of cannula 24. Outer portion 62 includes an external gripping surface that allows the user to hold handle 26. It will be understood that one or both of portions 62 and 64 may be indirectly or otherwise fixed or connected to ends 35, 49 of cannulas 22, 24. Portion 64 is rotatable within or with respect to portion 62 in the illustrated embodiment, so that when the user holds portion 62 (and thus cannula 22) he or she can rotate portion 64 (and thus cannula 24). Handle 26 may include a spring 66 and trigger mechanism 68, by which portion 64 may be cocked or primed by rotating it within portion 62 against the bias of spring 66 until trigger mechanism 68 catches, to hold portions 62, 64 (and their respective cannulas 22, 24) in a first relative position. When the hold is released (e.g. by activating trigger mechanism 68), the bias of spring 66 rotates portion 64 within or with respect to portion 62 to return to a second relative position.

As suggested above, portions 62 and 64 (with their respective cannulas 22, 24) can occupy one of two discrete relative positions in the illustrated embodiment. In a first relative position, portions 62 and 64 are arranged so that slits 40 and 56 are substantially or entirely aligned. In that configuration, there is a full opening formed from slits 40 and 56 that allows tissue through cannulas 22 and 24 and into lumen 48 of cannula 24. Triggering mechanism 68 (e.g. including a catch, detent mechanism, or similar structure) holds portions 62 and 64 (and cannulas 22, 24) in that first relative position when device 20 has been cocked. The second relative position in the illustrated embodiment has portions 62 and 64 arranged so that slits 40 and 56 do not overlap at all, so that lumen 48 of cannula 24 is not open to the outside at all. That second relative position is achieved in this embodiment by rotating portion 64 with cannula 24 through approximately the same arc subtended by one or both of slits 40, 56, e.g. about 180 degrees within portion 62 and cannula 22 in one embodiment, so that slit 40 faces the outer surface 44 of cannula 24 and slit 56 faces the inner surface 32 of cannula 22. In embodiments in which slits 40 and/or 56 are differently configured, the amount of arc through which portion 66 (and/or 68) travels in order to get from the first to the second relative configuration may be significantly less than or somewhat greater than 180 degrees. For example, in embodiments in which slits 40 and 56 are longitudinal, not diagonal or helical, portion 66 may need only be turned through 120 degrees, or through 120 to 150 degrees, in order to close the opening formed by juxtaposition of slits 40 and 56. A catch (e.g. detent or similar mechanism) may exist in or between portions 62 and 64 to hold them in the second relative position against inadvertent rotation. In embodiments described above in which spring 66 is provided, it biases portions 62 and/or 64 toward the second relative position, where slits 40, 56 are adjacent respective material of cannula 24 and 22, closing access to lumen 48 of cannula 24. As indicated above, rotating portion 64 with respect to portion 62 causes cannula 24 and slit 56 to move with respect to cannula 22 and slit 40, so that an opening into lumen 48 of cannula 24 is open or closed.

In some embodiments, inner cannula or member 24 is removable proximally while outer member 22 is in vivo, so as to take possession of the acquired specimen. For example, once a specimen is within lumen 48 of cannula 24, cannula 24 may be withdrawn from cannula 22, as by disengaging portion 64 from portion 62 in handle 26 and pulling portion 64 and cannula 24 out. Once the sample is retrieved from cannula 24, it can be re-inserted into cannula 22 for further sampling. The user may be assured that device 20 is adequately reassembled when, for example, tip 52 of cannula 24 engages or protrudes minimally from end 36 of cannula 22, when portion 64 engages an internal boss of portion 62, or when spring 66 and/or triggering mechanism 68 re-engage portion 64.

The distal ends or portions of one or both cannulas 22, 24 may possess echogenic and/or radiopaque materials or markers 80 to assist the user in visualizing the progress or positioning of device 20. Such materials or markers may be very helpful to the user when using device 20 under x-ray, ultrasound or other visualization techniques. For instance, the user is easily able to see when tip 52 and/or end 36 is at the edge of or just within the tissue area of interest, and thus knows to cock device 20 at that time. Likewise, further insertion of the cocked device 20 through the tissue can be easily monitored.

A particular use of device 20 for obtaining soft-tissue biopsy material is described below. It will be understood that similar uses in harder tissue, organs, or other parts of the body are also contemplated.

Device 20 is provided or placed in an insertion condition, which may depend on the insertion method desired. For example, device 20 may be directly inserted into the body to a position adjacent a biopsy location, or it may be moved into the body through a catheter (not shown) previously inserted to a position adjacent tissue to be biopsied. If device 20 is to be directly inserted through body tissue, the opening in device 20 formed by overlap of slits 40, 56 should be closed prior to insertion, so that entry of undesired tissue into device 20 during insertion is avoided. Thus, cannulas 22 and 24 are oriented with respect to each other so that tip 52 of cannula 24 engages or is adjacent distal end 36 of cannula 22, and slits 40 and 56 are rotationally or angularly offset with respect to each other. This orientation or configuration is exemplified by the second relative position of cannulas 22 and 24 (or handle portions 62 and 64) described above. In that condition, entrance to lumen 48 of cannula 24 is closed or blocked by the walls of cannulas 22 and/or 24. One or both of distal ends 36 and 50 thus provide a smooth, pointed distal end 36 for device 20, with generally smooth outer surface 30 of cannula 22 extending back from its distal end 36. The user identifies the location within a patient from which a tissue sample is desired, using x-ray, ultrasound, MRI or other diagnostic techniques, and consequently identifies a location on the skin through which device 20 is to be inserted in order to get to the location of the desired tissue. Device 20 is then inserted through the skin at the identified location. Insertion is continued toward the biopsy site with monitoring or direction of the distal end of device 20, as through ultrasound, x-ray or other visualization or observation techniques. With slits 40, 56 placed a distance proximal of ends 36, 50, the ends 36 and/or 50 may be placed in or just before the tissue of interest T prior to cocking. Placement can be checked by visualization techniques as previously noted, guaranteeing that slits 40, 56 (obtain the sample) will be within the sampling area.

If device 20 is to be inserted via a catheter, sheath or other conduit, the process can be quite similar. The conduit (not shown) is inserted toward the identified biopsy site so that its distal end is in or adjacent to the tissue of interest. In this case, an insertion condition for device 20 can be as noted above, but may advantageously be initially set so that slits 40, 56 are aligned rather than offset, to eliminate a step when device 20 is within the body. In such a case, cannulas 22 and 24 are oriented with respect to each other so that tip 52 of cannula 24 engages or is adjacent distal end 36 of cannula 22, and slits 40 and 56 are rotationally or angularly aligned with respect to each other. This orientation or configuration is exemplified by the first relative position of cannulas 22 and 24 (or handle portions 62 and 64) described above. In that condition, entrance to lumen 48 of cannula 24 is open, as is necessary for capturing tissue of interest. One or both of distal ends 36 and 50 thus provide a smooth, pointed distal end 36 for device 20, with generally smooth outer surface 30 of cannula 22 extending back from its distal end 36. The conduit having been placed (e.g. using x-ray, ultrasound, MRI or other diagnostic techniques) within the patient so that it ends in or adjacent the location from which a tissue sample is desired, device 20 is then inserted through the conduit. Insertion is continued toward the biopsy site, and monitoring or direction of the distal end of device 20, as through ultrasound, x-ray or other visualization or observation techniques, may be used.

As device 20 (e.g. distal ends 36 and/or 50 of cannulas 22, 24) arrives at or enters a proximal portion of the tissue to be sampled, forward insertion of device 20 is halted. Device 20 is then reconfigured by moving one or both of cannulas 22, 24 so that they are in the first relative position discussed above, in which slits 40 and 56 are aligned so that they are in an open position to provide an opening to lumen 48 of cannula 24. For example, in embodiments in which handle 26 includes spring 66 and holding or triggering mechanism 68, as discussed above, device 20 may be cocked or primed by turning handle portion 64 relative to handle portion 62 and against the bias of spring 66 until triggering mechanism 68 catches and holds portions 62 and 64 (and cannulas 22 and 24) in the second relative position, in which slits 40 and 56 are aligned and provide an opening into lumen 48 of cannula 24. Triggering mechanism 68 is sufficient to hold that second relative position until triggered.

With device 20 so primed, it is pushed forward (e.g. along the arrow in FIG. 5) so that slits 40, 56 enter into the sampling area. Preferably, device 20 is inserted a further distance such that slits 40 and 56 enter fully into the tissue desired to be sampled. For example, if the pre-cocking insertion places ends 36, 50 of cannulas 22, 24 just inside the sampling area, and slits 40, 56 begin 5 millimeters behind ends 36, 50 and extend longitudinally for 20 millimeters along cannulas 22, 24 device 20 may be moved further forward approximately 25 millimeters to ensure the entirety of slits 40, 56 are within tissue to be sampled.

As device 20 is inserted through the tissue of interest, placing generally radially outward pressure on it, the tissue reacts by pressing against the outer surface 30 of cannula 22. A sample portion S of the tissue of interest enters slits 40 and 56, and passes into lumen 48 of cannula 24. Sharp edges 42 and/or 58 along slits 40 and 56 cut a profile along tissue that engages them as the tissue travels along them. As previously noted, in some embodiments, the length of travel of primed device 20 through the sampling area is at least approximately the length that slits 40 and 56 travel along the longitudinal axis of cannulas 22, 24. However, it will be understood that a substantially greater or lesser length of travel of primed device 20 can be used, since a greater length of travel will simply push tissue further into lumen 48 of cannula 24 beyond the end of slit 56, and a lesser length of travel will provide a smaller amount of tissue.

It will be understood that the cocking step may occur before or after device 20 has been fully inserted to its final location in the body. If cocking (to place slits 40, 56 in the first (open) relative position) occurs prior to final placement, then as device 20 is advanced to its final location tissue of interest can enter or "flow" into lumen 48, with a profile cut by sharpened edges noted above. If cocking occurs after final placement, so that no tissue enters lumen 48 prior to final placement, then tissue can recoil or press into lumen 48 when slits 40, 56 are placed in the first (open) relative position.

With device 20 held steady, handle 26 is triggered. By triggered, it is meant that portions 62 and/or 64 of handle 26 are released from being held in the open, first relative position with respect to each other and rotated (or allowed to rotate) with cannulas 22, 24 back to the second (closed) relative position, as under the bias of a spring. In the illustrated embodiment, for example, activating or releasing triggering mechanism 68 causes cannula 24 to rotate (due to bias of spring 66) within cannula 22, which is held stationary by the user's grip on handle 26 (e.g. on portion 62). In spring-biased embodiments, the rotation of cannula 24 is quite fast. Accordingly, as cannula 24 rotates, its sharpened edge(s) 58 moves through the tissue passing through slit 56. Tissue sample S within lumen 48 of cannula 24 is thus sheared free from adjacent tissue in the sampling area and is encircled principally by cannula 24. Cannula 22 covers slit 56 in cannula 24 to provide a closed container for the tissue.

With the sample S captured in lumen 48, it is withdrawn from the body and placed in a dish or container for study or assaying. In one example, the entire device 20 is removed from the patient, with cannulas 22 and 24 in the closed relative position. The relatively close fit of the cannulas result in no undesired tissue entering device 20. Once device 20 is removed from the patient, cannula 22 can be rotated (as by rotating portion 64 of handle 26) to the open position, exposing the tissue within lumen 48 of cannula 24. The user then extracts the tissue from lumen 48. In another example, outer cannula 22 may be retained in the patient while inner cannula 24 is withdrawn through outer cannula 22. Handle portions 62 and 64 are disengaged from each other, and portion 64 (with cannula 24) is pulled out. A container for the tissue sample should be held close to handle 26, as open slit 56 of cannula 24 will exit cannula 22 in this example, leaving no cover for slit 56 and the tissue within lumen 48. As before, the user extracts the tissue from lumen 48. Following extraction of the tissue sample, by either method noted above or by other methods, device 20 can be re-inserted into the patient (and/or cannula 24 can be re-inserted into cannula 22, with portions 62, 64 re-engaged with each other as well as any spring 66 and triggering mechanism 68), and device 20 can be re-used at the prior sampling location or at another location.

This device provides a simpler, less expensive, and more repeatable mechanism to access, cut, and retrieve tissue of interest for testing through a minimally-invasive biopsy procedure. Because of the rotating actuation and cutting mechanism the device is placed exactly into the tissue in question without concern for incorrect placement of the tip distally (i.e. too far through the tissue of interest) or proximally (not far enough toward or in tissue of interest). The result of such incorrect placements is that the biopsy retrieves a sample that includes a significant portion of undesired (e.g. normal) tissue. Since slits 40, 56 occupy less than half of the circumference of their respective cannulas 22, 24, penetrating the tissue of interest with device 20 in the open position results in cutting a profile through the tissue of interest that is more than 50% percent of the final cut in the tissue. The rotating cutter (internal cannula 24) finishes shearing the tissue portion completely (i.e. completes the profile to make the final cut), to obtain full 360 degree tissue sampling regardless of the consistency of the tissue.

Figure 8B:
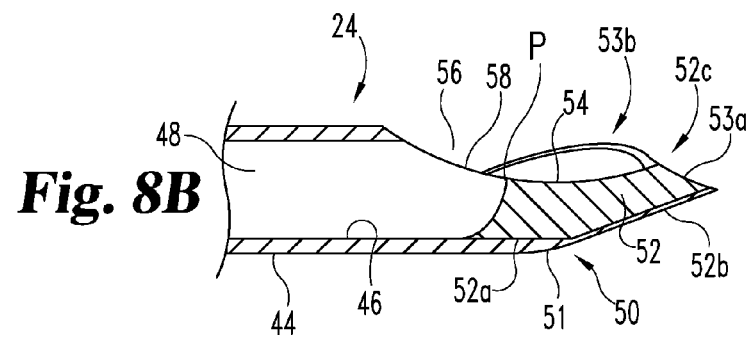
FIG. 8B is a partial cross-section of the embodiment of structure shown in FIG. 8A.
Figure 8A:
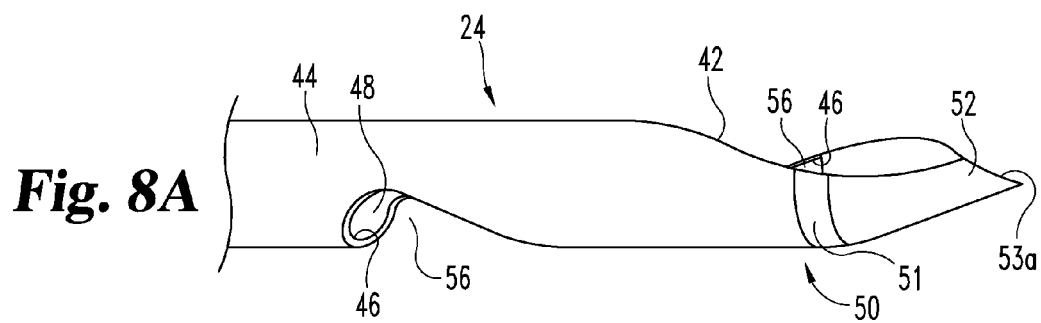
FIG. 8A is a side view of a portion of structure that can be used in the embodiment of FIG. 1.

With respect to the above embodiments, it is noted that the configuration of the tip 52 of inner cannula 24 may be fashioned in a number of ways. Referring particularly to FIG. 8A-B, there is shown a cannula 24 featuring outer wall 44 and inner wall 46 bounding lumen 48. In this embodiment, distal end 50 of cannula 24 has a beveled surface 51, of the same or similar configuration as surface 38 of cannula 22, described above. Tip 52 is initially a piece separate from cannula 24, and is inserted into lumen 34 at the distal end 36 of cannula 24. A substantially cylindrical portion 52a of tip 52 is fixed to cannula 24 by interference fit, by mechanical joining (e.g. tongue and groove), by adhesive, by welding or by other joining methods. A first lateral portion 52b of tip 52 is flat or conical in surface, generally complementary to the beveled end 38 of cannula 22. A second lateral portion 52c is generally opposite of first lateral portion 52b in this embodiment, and includes an end part 53a that is generally flat or conical in surface and generally complementary to the beveled end 51 of cannula 24 and/or beveled end 38 of cannula 22. It also includes a more proximal part 53b that forms a part of or is complementary to slit 56 of cannula 24. As viewed in cross-section (FIG. 8B), an edge 54 of proximal part 53b of tip 52 meets an edge 58 of slit 56 in a smooth curve (as at point P in FIG. 8B). Proximal part 53b may form a deepening entry into slit 56, as where an internal surface of tip 52 slopes into lumen 48 from the junction between proximal part 53b and end part 53a, or tip 52 may be a partially or fully hollow, with an open space. As seen in FIG. 8A, slit 56 has one end along one side of a distal portion cannula 24 and a second end in a more proximal portion of cannula 24 and approximately 180 degrees around from the more distal end. It will be understood that, as in above-noted embodiments, slit 56 may extend a different amount around cannula 24, e.g. about a full 360 degrees around.

Figure 9B:
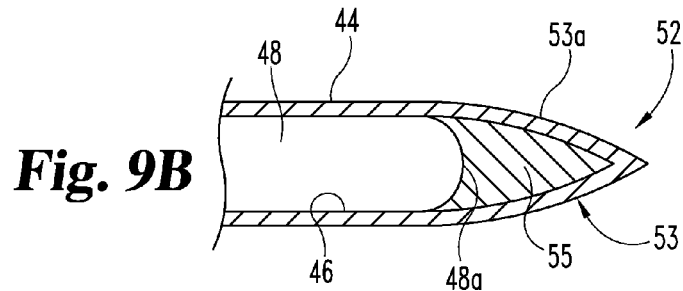
FIG. 9B is a partial cross-section of the embodiment of structure shown in FIG. 9A.
Figure 9A:
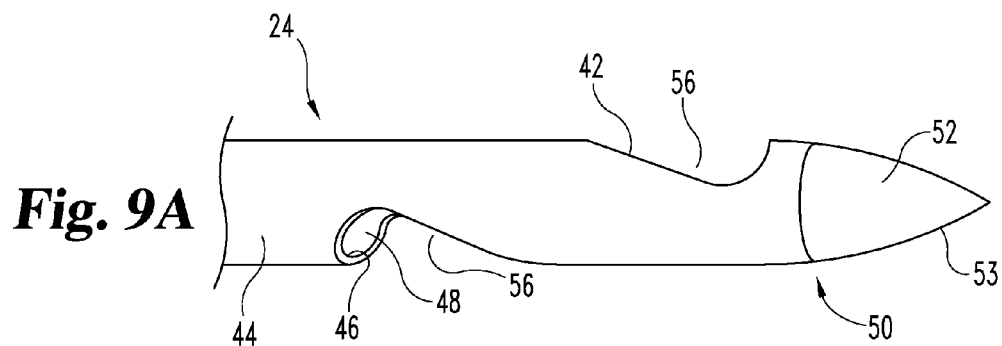
FIG. 9A is a side view of a portion of structure that can be used in the embodiment of FIG. 1.

FIGS. 9A-B indicate a tip 52 fashioned monolithically with the rest of cannula 24, featuring a closed end 53 with a substantially conical exterior surface 53a. In this embodiment, tip 52 has a wall that is a continuation of the wall of cannula 24, and thus has an interior space 48a that is a continuation of lumen 48. Substantially all of space 48a is filled in this embodiment by a firmly fixed block or boss 55. Block 55 may be made of a sturdy material so as to act as a support for otherwise hollow tip 52 during use, to force tip 52 through tissue during the biopsy process. In particular embodiments, where cannula 24 is of a metallic substance, block 55 may be of a non-metallic substance or of the same metallic substance as cannula 24.

Figure 10B:
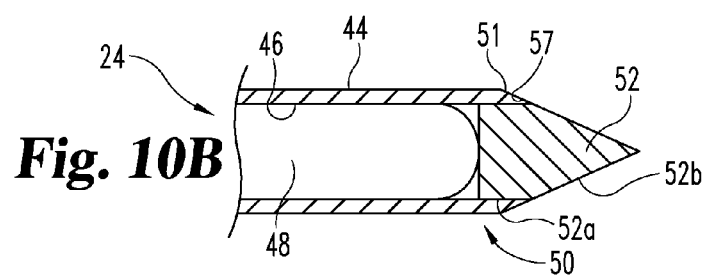
FIG. 10B is a partial cross-section of the embodiment of structure shown in FIG. 10A.
Figure 10A:
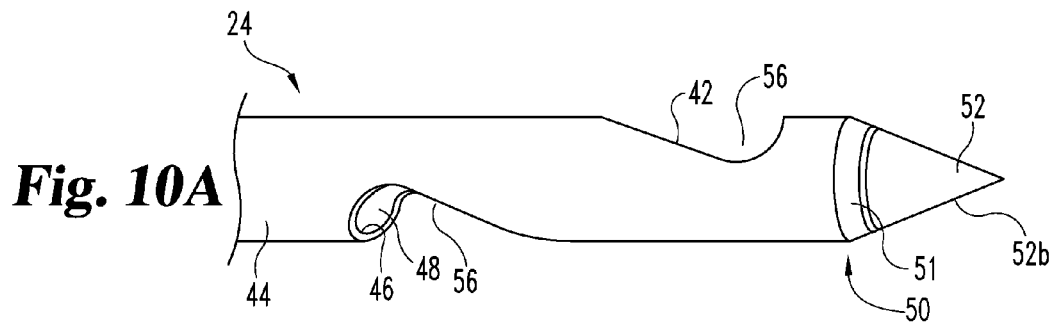
FIG. 10A is a side view of a portion of structure that can be used in the embodiment of FIG. 1.

FIGS. 10A-B indicate a tip 52 fitted into an open distal end 50 of cannula 24. In this embodiment, distal end 50 has a beveled surface 51 that slopes inward around the entire circumference of cannula 24, as indicated in embodiments discussed above. Tip 52 is made separately from cannula 24 and is then joined, as discussed previously. In this embodiment, tip 52 has a relatively short cylindrical portion 52a that is fitted into lumen 48 and fixed there as exemplified in above-noted embodiments. Tip 52 is conical in the exterior of its distal-most portion 52b, and solid in this embodiment. The conical exterior of this embodiment of tip 52 may be of the same angle as the beveled surface 51 of cannula 22 and/or surface 38 of cannula 24. A substantially continuous conical surface is observed from tip 52 to surface 51 of cannula 24 when tip 52 is inserted in lumen 48 so that the junction of its conical and cylindrical portions 52b and 52a are adjacent or adjoining the sharp circular end of beveled surface 51 of cannula 24. Tip 52 may have a slight ledge or boss 57 between conical surface 52b and cylindrical portion 52a that abuts against of beveled surface 51. In such embodiments, boss 57 prevents tip 52 from being pushed further into lumen 48 during use of needle 20. Such an embodiment may be used in cases where cylindrical portion 52a has a snug or interference fit with cannula 24 in lumen 48, and can obviate the need for adhesives, welding or similar joining methods to be applied between tip 52 and cannula 24. With boss 57 in tip 52, the conical surface of tip 52 may overlap beveled surface 51 of cannula 24 slightly. A smooth transition between tip 52 and beveled surface 51 is desirable to limit or eliminate scores or gouges to tissue as it passes over tip 52.

Figure 11A:
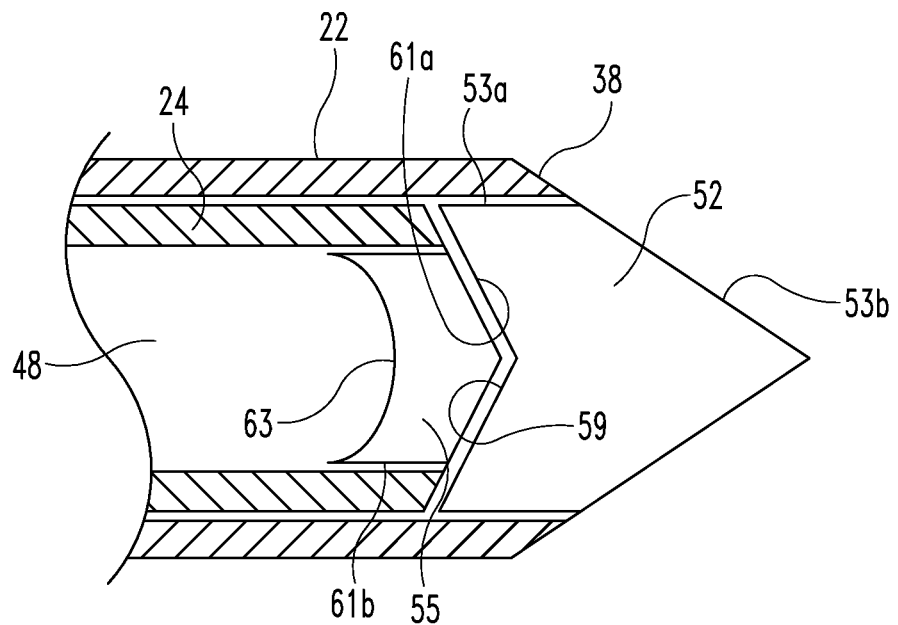
FIG. 11A is a partial cross-section of a portion of structure that can be used in the embodiment of FIG. 1.
Figure 11B:
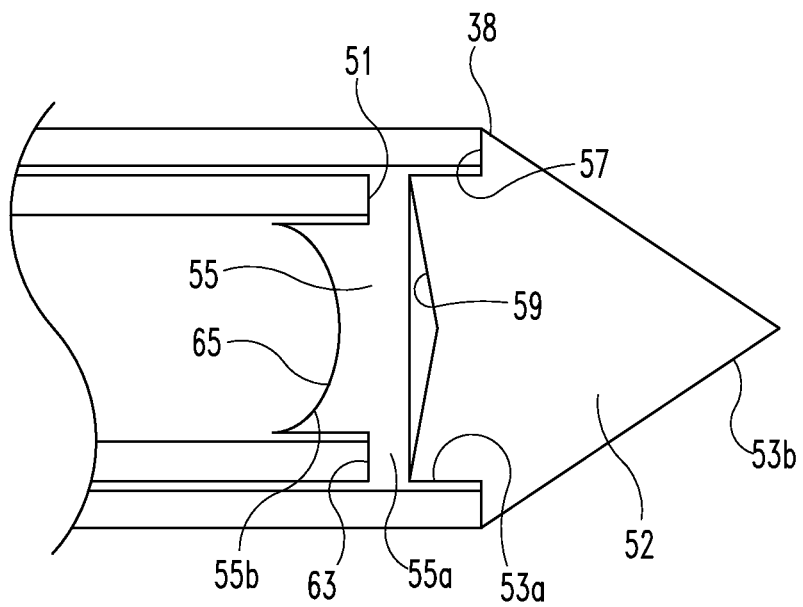
FIG. 11B is a partial cross-section of the embodiment of structure shown in FIG. 11A.

In the embodiments of FIGS. 11A-B, outer cannula 22 is shown with inner cannula 24 inside its lumen 34, each having separate tip structures. In FIG. 11A, cannula 22 has a beveled surface 38 at its distal end which points inward all around its circumference. This embodiment of tip 52 is much like the embodiments shown in FIGS. 8B and 10B, with a distal conical exterior surface 53b and a proximal cylindrical exterior surface 53a. Conical exterior surface 53b matches the bevel of surface 38 of cannula 22, and cylindrical surface 53a is fixed to the interior surface 32 of cannula 22, as by interference fit, mechanical joining, adhesive fixation, welding or the like. Tip 52 includes a conical indent 59 opposite conical exterior surface 53b, i.e. within lumen 34 of cannula 22 and facing proximally along lumen 34. Indent 59 has its center along the central longitudinal axis of cannula 22 (and cannula 24 of needle 20) in this embodiment.

Tip 55 in FIG. 11A is also much like the tip in FIG. 10B (and the tip described immediately above), and is fixed to the interior of cannula 24 as indicated previously. A substantially cylindrical surface 61a fits in lumen 48 of cannula 24, and a distal conical surface 61b is complementary to indent 59 of tip 52, so that tip 55 can mate with tip 52. That mating fit provides guidance with minimal friction as one or both of cannulas 22, 24 are rotated around their common central longitudinal axis with respect to each other. A rearward (or proximal) surface 63 of tip 55 is within lumen 48 of cannula 24 and faces the space in which tissue will be captured (as described above).

In FIG. 11B, tip 52 is provided for cannula 22, which in this embodiment has non-beveled end surfaces 38. Tip 52 is similar to the tip shown in FIG. 10B, with a distal conical exterior surface 53b, a proximal cylindrical exterior surface 53a for closely fitting in lumen 34 of cannula 22, and a ledge or boss 57 between surfaces 53a and 53b. Proximal surface 53a is fixed to cannula 22 via an interference fit, mechanical connection, adhesive, welding, or the like. In that embodiment, the thickness of boss 57 is at least approximately the same as the wall thickness of cannula 22, so that when cylindrical surface 53a is within lumen 34, the radially-outermost extent of conical surface 53b is at the same distance from the central longitudinal axis as the outer surface 30 of cannula 22. A rearward (or proximal) surface 59 of tip 52 is within lumen 34 and faces proximally along lumen 34. Rearward surface 59 may have an indented conical configuration (as with surface 59 in FIG. 11A), or a substantially planar surface perpendicular to the central longitudinal axis, in particular embodiments.

Tip 55 is provided for cannula 24, which also in this embodiment has non-beveled end surfaces 51. Tip 55 is a disc-like structure having a distal portion 55a that is at least approximately cylindrical and a proximal portion 55b that is at least approximately cylindrical and smaller in radius than distal portion 55a. Proximal portion 55b is fixed to cannula 24 via an interference fit, mechanical connection, adhesive, welding, or the like. A boss or ledge 63 is between portions 55a and 55b, so that distal portion 55a may be thought of as providing a flange from proximal portion 55b. The thickness of boss 63 is at least approximately the same as the wall thickness of cannula 24, so that when cylindrical surface 55b is within lumen 48, the outer edge of distal portion 55a is at least approximately flush with the outer surface 44 of cannula 22. Tip 55 includes a surface 65 that generally faces the space in which the biopsy sample will reside when taken. Tip 55 provides support for the distal end of cannula 24, and acts as a buffer between cannula 24 and tip 52 in cannula 22, with tip 55 able to move with cannula 24 relative to cannula 22.

While members 22 and 24 are principally identified as "cannulas" herein, it should be recognized that other structures could be used. For example, an inner member 124 could be in the form of a wire with a cut-out 156 that corresponds to slit 40 of outer cannula 22. Cut-out 156 operates in similar fashion to slit 56 and lumen 48 of cannula 24, providing a location for tissue to enter and be retained. As with cannula 24, wire member 124 may have sharpened edges 158. Other parts and relationships noted above with respect to examples of cannula 24 may be present in member 124.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected. It will be understood that features or attributes noted with respect to a specific embodiment may be used or incorporated into other embodiments of the structures and methods disclosed.

What is claimed is:

1. An apparatus for obtaining a biopsy sample, comprising:
   a first cannula having a lumen surrounded by a lumen wall, said first cannula having a distal end with a sharp edge, said first cannula further having a slit beginning at a point proximal of said distal end and extending proximally, said wall between said distal end and said slit being smooth;
   a second cannula within lumen of said first cannula, said second cannula having a lumen and a closed distal end tapering to a point, said second cannula having an outer diameter such that said second cannula has a close and rotatable fit with said wall of said first cannula, said second cannula further having a slit beginning at a point proximal of said tapering distal end surface and not in the tapering surface and bounded by at least one sharpened edge,
   wherein said cannulas have a first open relative position, in which said slits define an open passage from the exterior of said first cannula to the lumen of said second cannula, and a second closed position, in which said slits are rotationally offset from each other, and wherein change between said first position and said second position is accomplished by rotation of at least one of said cannulas, and wherein said slits are helical and extend about 360 degrees around said respective first and second cannulas.

2. The apparatus of claim 1, wherein said slits are substantially congruent to each other, so that when said cannulas are in said first open relative position, said slits are substantially exactly aligned along their entireties.

3. The apparatus of claim 2, wherein said first cannula has a central longitudinal axis, and said second cannula is rotatable around said central longitudinal axis.

4. The apparatus of claim 3, wherein said slits are non-parallel to said central longitudinal axis.

5. The apparatus of claim 4, wherein said slits are diagonal or helical with respect to said central longitudinal axis.

6. The apparatus of claim 3, wherein said slits are parallel to said central longitudinal axis.

7. The apparatus of claim 1, wherein said distal end of said first cannula is closed, said cannulas being configured so that said tapering distal end of said second cannula can engage said closed distal end of said first cannula, and so that when said tapering distal end engages said closed distal end of said first cannula, said slits are relatively positioned in one of: said first open relative position, said second closed relative position, and a position between said first and second relative positions.

8. The apparatus of claim 1, further comprising a handle having an inner portion and an outer portion, said outer portion fixed to said first cannula and said inner portion fixed to said second cannula, wherein rotation of at least one of said handle portions with respect to the other shifts said cannulas toward one of said relative positions.

9. The apparatus of claim 8, wherein said inner handle portion is rotatable with respect to said outer handle portion, and wherein said inner handle portion is spring-biased, said bias tending to hold said cannulas in said second relative position.

10. The apparatus of claim 9, further comprising a triggering mechanism adapted to hold said inner handle portion in a cocked position against said bias, wherein said cocked position corresponds to said cannulas being in said first open relative position, and wherein release of said triggering mechanism allows said bias to rotate said second cannula within said first cannula.

11. The apparatus of claim 1, wherein at least one of said distal end of said first cannula and said distal end of said second cannula includes a marker that is at least one of radiopaque and echogenic.

12. An apparatus for obtaining a biopsy sample, comprising:
a first tubular member having a distal end and a slit a distance proximally away from said distal end;
a second tubular member rotatably positioned within said first tubular member and having a slit with at least one sharpened lateral edge; and
a handle having a first portion attached to said first tubular member and a second portion attached to said second tubular member, said handle including a spring-bias and a triggering mechanism,
wherein said apparatus has a first uncocked configuration in which said slits do not overlap, and a second cocked configuration in which said second tubular member and second handle portion are rotated from said first configuration against the bias so that said slits overlap and said triggering mechanism maintains said second configuration, and wherein activation of said triggering mechanism when said apparatus is in said second configuration results in said bias rotating said second tubular member within said first tubular member to said first configuration, and wherein said slits are helical and extend about 360 degrees around said respective first and second tubular members.

13. The apparatus of claim 12, wherein at least one of said slits is diagonal or helical.

14. The apparatus of claim 12, wherein in said second configuration the entirety of said slit of said second tubular member overlaps said slit of said first tubular member.

15. The apparatus of claim 12, wherein said second tubular member is adapted to be entirely withdrawn longitudinally from within said first tubular member to retrieve a sample within said second tubular member.

16. The apparatus of claim 12, wherein each of said slits has a length measured along a longitudinal axis of their respective tubular members and a width measured perpendicular to the longitudinal axis of their respective tubular members, and wherein said widths are substantially constant and subtend an arc of more than 90 degrees but less than 180 degrees of their respective tubular members.

17. The apparatus of claim 12, wherein said slit of said first tubular member has at least one lateral edge that is sharpened, and said sharpened lateral edge of said slit of said first tubular member faces said sharpened lateral edge of said slit of said second tubular member when said apparatus is in said second cocked configuration.

18. An apparatus for obtaining a biopsy sample, comprising:
a first cannula having a central lumen surrounded by a lumen wall, said first cannula having a distal end with a sharp edge, said first cannula further having a diagonal or helical slit beginning at a point proximal of said distal end and extending proximally, said wall between said distal end and said slit being smooth;
a second cannula having a lumen and a closed distal end tapering to a point, said second cannula being positioned within said lumen of said first cannula so that said tapering distal end of said second cannula is within or extending from said distal end of said first cannula, said second cannula having an outer diameter such that said second cannula has a close and rotatable fit with said wall of said first cannula, said second cannula further having a diagonal or helical slit beginning at a point proximal of said tapering distal end and bounded by at least one sharpened edge,
wherein said cannulas have a first open relative position, in which said slit of said first cannula lies over the entirety of said slit of said second cannula and said slits define an open passage from the exterior of said first cannula to the lumen of said second cannula, and a second closed position, in which said slits are rotationally offset from each other and no part of said slots face each other, and wherein change between said first position and said second position is accomplished by rotation of said second cannula with respect to said first cannula; and
a handle having a first portion fixed to said first cannula and a second portion fixed to said second cannula, said second portion rotatable with respect to said first portion to rotate said second cannula with respect to said first cannula, said handle including a spring biasing said second handle portion so that said cannulas are in said second closed relative position and a triggering mechanism adapted to hold one or both of said handle portions against the bias of the spring so that said cannulas are in said first open relative position.

19. The apparatus of claim 18, wherein said distal end of said first cannula is closed, and said tip of said second cannula abuts said distal end of said first cannula.

20. The apparatus of claim 18, wherein said distal end of said first cannula is open, and said tip of said second cannula faces outward from said distal end of said first cannula and forms with said distal end of said first cannula a leading insertion end of said apparatus.

21. The apparatus of claim 18, wherein at least one of said distal end of said first cannula and said tip of said second cannula includes a marker that is at least one of radiopaque and echogenic.

* * * * *